United States Patent

Pistorius

[11] 4,057,586
[45] Nov. 8, 1977

[54] PROCESS FOR THE MANUFACTURE OF HYDROQUINONE DIMETHYL ETHERS

[75] Inventor: Rudolf Pistorius, Wehrheim, Germany

[73] Assignee: Hoechst Aktiengesellschaft, Frankfurt am Main, Germany

[21] Appl. No.: 734,455

[22] Filed: Oct. 21, 1976

[30] Foreign Application Priority Data

Oct. 23, 1975   Germany ............................ 2547464

[51] Int. Cl.² .............................................. C07C 41/00
[52] U.S. Cl. ................................ 260/613 D; 204/72; 204/59 R
[58] Field of Search ................................... 260/613 D

[56] References Cited
U.S. PATENT DOCUMENTS 1,919,580   7/1933   Wagner et al. ................ 260/613 D Primary Examiner—Bernard Helfin
Attorney, Agent, or Firm—Curtis, Morris & Safford

[57] ABSTRACT

Hydroquinone dimethyl ethers of the formula

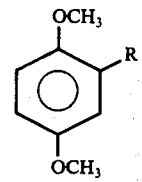

wherein R is H, an alkyl group having from 1 to 4 carbon atoms or halogen are prepared by catalytical hydrogenation of benzoquinone tetramethyl diketals of the formula

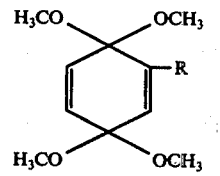

wherein R has the same meaning as in formula I
at a temperature from about 0° to +150° C. As the starting compounds II may be obtained by anodic oxidation of benzene and the corresponding benzene derivatives in methanol hydroquinone dimethyl ethers I used, for example for the manufacture of dyestuffs, may be obtained in simple manner by using benzene or the corresponding benzene derivative as starting products.

7 Claims, No Drawings

PROCESS FOR THE MANUFACTURE OF HYDROQUINONE DIMETHYL ETHERS

Hydroquinone dimethyl ether and hydroquinone dimethyl ethers substituted on the aromatic nucleus, especially chlorinated hydroquinone dimethyl ethers, are valuable intermediates, especially for the preparation of dyestuffs. On an industrial scale they are nearly exclusively prepared from hydroquinone as starting product, which compound is conventionally prepared from p-benzoquinone. The latter in its turn is not present as such, but must firstly be synthesized.

As the above indicated method of synthesizing is rather complicated and unsatisfactory, especially when performed on an industrial scale, it was desirable to find a technically simpler process for the manufacture of hydroquinone dimethyl ethers and derivatives thereof substituted on the aromatic nucleus. The present invention has solved this task by catalytically hydrogenating p-benzoquinone tetramethyl-diketals.

The present invention consequently provides a process for the manufacture of hydroquinone dimethyl ethers of the formula

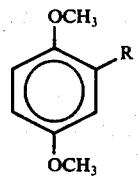

wherein R is hydrogen, an alkyl group having from 1 to 4 carbon atoms, preferably the methyl group, or halogen, especially Cl or F, which comprises hydrogenating p-benzoquinone tetramethyl diketals of the formula

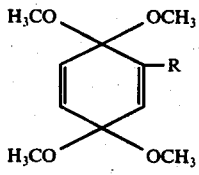

wherein R has the same meaning as in formula I, catalytically, in a solvent conventionally used for catalytical hydrogenations, in the presence of a noble metal catalyst and optionally a weak acid, at a temperature from about 0° to +150° C.

The process to be carried out in simple manner according to the following equation

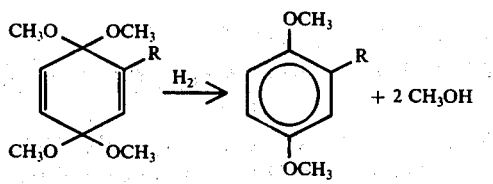

moreover has the important advantage that the starting compounds II may also be prepared in simple manner without passing via the p-benzoquinone stage.

The p-benzoquinone tetramethyl diketal of the formula II substituted on the nucleus, wherein R is H, may be obtained, for example, by anodic oxidation of anisol in methanol/KOH (according to N. L. Weinberg and B. Belleau, J. Am. Chem. Soc. 85 (1963) 2525-26; Tetrahedron Letters 29 (1973), 279-85).

The unsubstituted p-benzoquinone tetramethyl diketals as well as those substituted by the radicals R indicated above are advantageously prepared according to the electrochemical process disclosed in DOS No. 2,460,754. According to this process benzene or anisol optionally substituted in ortho- or meta-position by an alkyl group having from 1 to 4 carbon atoms or by halogen is oxidized anodically in methanol containing less than about 5% by weight of water as well as about 0.2 to 15% by weight, calculated on the electrolyte, of at least one ammonium or alkali metal fluoride, perchlorate, nitrate, tetrafluoroborate, hexafluorosilicate, hexafluorophosphate or p-toluenesulfonate as conducting salt as well as optionally from about 0.5 to 10% by weight, also calculated on the electrolyte, of a difficultly oxidizable base, at a pH from 7 to about 10, at a known anode made from graphite, a metal selected from the platinum group or alloys thereof or from $PbO_2$, at a temperature in the range from about $-20°$ to $+60°$ C, preferably from about 0° to $+40°$ C and especially from about 20° to 35° C. Preferred conducting salts are $NaClO_4$ and KF and the difficultly oxidizable base used preferably is especially 2,6-lutidine.

The electrochemical reaction may be carried out in an undivided cell as well as in a cell divided into a cathode and an anode space by any of the conventional diaphragms. It may also be performed batchwise, semicontinuously or fully continuously. The current quantity applied should be at least equivalent to the quantity of the starting material to be oxidized, i.e. when using benzene corresponding to a 6 electrodes reaction, 6 faraday/mole, when using anisol, 4 faraday/mole. Generally the current quantity is advantageously used in a considerable excess amounting for example up to about 4 times, preferably up to 1.5 to 3 times of the theoretically required quantity.

The chosen current density per $dm^2$ of the anode surface may be in the usual range from about 0.5 to about 40 $A/dm^2$, preferably from about 5 to 20 $A/dm^2$. The cell voltage results from the current intensity, the conductivity and the dimensions of the cell. It is generally from about 4 to 30 volts.

This process permits preparing p-benzoquinone tetramethyl ketal from benzene and anisol and the corresponding substituted p-benzoquinone tetramethyl ketals from the anisols substituted in ortho- or meta-position. Thereby the reaction mixture is worked up in known manner, for example by distilling off methanol and the unreacted starting product and by subsequently distilling the crude product under an adequately reduced pressure or by extraction and/or crystallization of the products of the invention.

In the process of the invention the starting material II is firstly dissolved in a solvent conventionally used for catalytic hydrogenations. The solvents may be of commercial grade purity. Solvents having a proton activity superior or equal to that of tetrahydrofurane, dioxane or ethylacetate and not exceeding that of glacial acetic acid, are used preferably. There may be mentioned particularly solvents or mixtures of solvents having pKS values from about 25 to about 4.7. The desired acidity may also be attained thereby by mixing different acidic solvents, especially by the addition of weak acids, for example propionic acid or acetic acid. Suitable solvents are, for example, ethers such as diethyl ethers, diisopropyl ethers, tetrahydrofurane, dioxane etc., alcohols such as methanol, ethanol, propanol, cyclohexanol etc., weak organic acids, for example acetic acid, propionic acid, butyric acid etc., esters, for example methylacetate, ethylacetate, ethylpropionate etc. Propionic acid and propionic acid-containing solvents are preferably used as hydrogenation medium. The latter may contain from 0.05 to 99.95% by weight of propionic acid, depending on their miscibility. The concentration of ketal II in the solvent or the mixture of solvents may be in the range from about 0.05 to 85% by weight, depending on the solubility; generally there are used solutions of about 10 to 30% strength.

Suitable catalysts are noble metal catalysts conventionally used for catalytic hydrogenations, especially such based on metals of group VIII of the Periodical Table, in a pure form as well as in form of their oxides or applied on carrier materials such as active carbon. Among the noble metals of group VIII comprising Ru, Rh, Pd, Os, Ir and Pt Pd and Pt are preferably used. The catalysts are used in the conventional amounts, preferably from about 0.05 to 0.2% by weight, calculated on the starting compound used of formula II.

The temperature at which the hydrogenation according to the invention may be performed may vary from about 0° to +150° C. This temperature range is not absolutely critical. A range from about 10° to 100° C, especially from about 15° to 40° C is preferably applied.

The hydrogenation already takes place under a hydrogen pressure from 0.2 to about 200 atmospheres and more. A pressure from about 1 to 100 atmospheres, especially from about 10 to 50 atmospheres is preferably used.

Suitable hydrogenation devices are apparatuses conventionally used for such reactions, for example an autoclave provided with a shaker or corresponding glass or enamel vessels provided with a shaking device. After consumption of the stoichiometrical quantity of $H_2$ the reaction mixture is worked up in known manner, for example by filtering off the catalyst, by distilling off the solvent and methanol formed during the reaction as well as by subsequently distilling or crystallizing the hydroquinone dimethyl ether obtained.

The uniform reaction course, especially in the hydrogenation of monochloro-p-benzoquinone tetramethyl diketal yielding monochlorohydroquinone dimethyl ether, is especially surprising, as it was to be expected especially in the latter case that the ring-substituted Cl atom would be removed by hydrogenation. In accordance with the uniform reaction course the yields of the desired hydroquinone dimethyl ethers are very good.

The following examples illustrate the invention:

EXAMPLE 1 a. Preparation of p-benzoquinone tetramethyl diketal

In a double-walled cell cooled with water having a volume of about 750 ml 20 g of benzene dissolved in an electrolyte consisting of 650 ml of methanol/7.5 g of KF were electrolyzed at a cylindrical platinum wire-gauze electrode (diameter 4 cm, height 4 cm) as anode and a tube made from Cr-Ni steel (V4A) having a diameter of 12 mm as a cathode, which was separated by the anode by a porous polyethylene tissue, with a current intensity of 3.5 A and a voltage of about 22 volts at a temperature of 22° C until 18.5 Ah had passed. Stirring was effected by means of a magnetic type rod agitator fixed at the bottom of the vessel.

Methanol as well as benzene were used in a technically pure quality. For working up, methanol and benzene were distilled off and 8 g of benzoquinone tetramethyl ketal (melting point 43° C) were obtained from the crude product obtained (16 g) by distillation at a temperature from 86° to 89° C and under a pressure of 0.3 mm Hg in a yield of 83% by weight.

b. Preparation of hydroquinone dimethyl ether according to the invention 100 ml of propionic acid and 0.5 g of Pd applied on active carbon (5% by weight of Pd) and 20.2 g (0.1 mol) of p-benzoquinone tetramethyl-diketal were introduced into an autoclave having a volume of 150 ml. Hydrogenation was performed for 3 hours under a hydrogen pressure of 50 atmospheres and at a temperature of +25° C. The $H_2$ absorption was about 2.3 liters (under normal conditions of temperature and pressure). The thin-layer chromatographic and gas chromatographic examination revealed hydroquinone dimethyl ether as unique reaction product. The yield determined by gas chromatography was about 95%, calculated on diketal used. 12.3 g of hydroquinone dimethyl ether, corresponding to a yield of 87% of the theory, were obtained by fractional distillation.

EXAMPLE 2 a. Preparation of monochloro-p-benzoquinone tetramethyl ketal 35 g of chloranisol were electrolyzed under the same conditions as in Example 1 until 11 Ah had passed. The yield of monochloro-p-benzoquinone tetramethyl ketal was likewise about 83% of the theory. The melting point of the product was about 64° C.

b. Preparation of monochlorohydroquinone dimethyl ether according to the invention In analogous manner to Example 1(b) 20 g of chlorobenzoquinone tetramethyl diketal were dissolved in 150 ml of ethylacetate and hydrogenated under a hydrogen pressure of 50 atmospheres in the autoclave after the addition of 0.5 g of Pd/C (5% by weight of Pd). The temperature was maintained at 20° C. The $H_2$ absorption was about 2 liters(under normal conditions of pressure and temperature). The distillation yielded 11.5 g of crude product containing 95.6% of chlorohydroquinone dimethyl ether according to the gas chromatographic analysis, which corresponds to a yield of 73% of the theory.

EXAMPLE 3 a. Preparation of methyl-p-benzoquinone tetramethyl ketal 35 g of m-cresyl ether were electrolyzed under the same conditions as in Example 1(a) until a passage of 22.8 Ah. A current efficiency of 30.7% could be determined by iodometrical analysis. The distillation yielded besides unconsumed starting material 7.8 g of methyl-p-benzoquinone tetramethyl ketal at a temperature of about 86° C and under a pressure of 0.6 mm Hg, which compound was in a liquid state at room temperature and crystallized when placed in a refrigerator (melting point 6° C).

b. Preparation of methylhydroquinone dimethyl ether according to the invention

As in Example 1(b) 9 g of methylbenzoquinone tetramethyl ketal were dissolved in 100 ml of ethylacetate, mixed with 1 g of propionic acid and 0.5 g of Pd/C (5% by weight of Pd) and hydrogenated under a hydrogen pressure of 100 atmospheres in the autoclave for 1.5 hours, at room temperature. After filtration of the catalyst and distillation of the solvent there remained 7.5 g of crude product consisting of 5.25 g of methylhydroquinone dimethyl ether according to the gas-chromatographic analysis, which corresponds to a yield of 82% of the theory.

NMR $\tau = 3.0-3.65$ 3H,m; $\tau = 6.26-6.3$,6H,2s; $\tau = 7.68$, 3H,s.

What is claimed is:

1. Process for the manufacture of hydroquinone dimethyl ethers of the formula

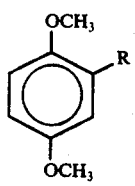

I, wherein R is hydrogen, an alkyl group having from 1 to 4 carbon atoms or hydrogen, which comprises hydrogenating catalytically p-benzoquinone tetramethyl diketals of the formula

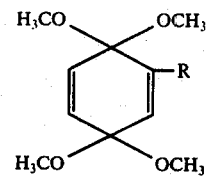

II, wherein R has the same meaning as in formula I, in the presence of a noble metal catalyst at a temperature from about 0° to +150° C.

2. Process as claimed in claim 1, wherein R is H, CH$_3$, Cl or F.

3. Process as claimed in claim 1 wherein a solvent is used for the catalytical hydrogenation having a pKS value from about 25 to about 4.7.

4. Process as claimed in claim 3, which comprises using as solvent propionic acid or a propionic acid-containing mixture of solvents.

5. Process as claimed in claim 1 which comprises using as noble metal catalysts Pd or Pt.

6. Process as claimed in claim 1 wherein the temperature during the catalytical hydrogenation is from about 10° to 100° C.

7. Process as claimed in claim 1 which comprises performing the catalytical hydrogenation under a hydrogen pressure from about 1 to 100 atmospheres.

* * * * *